United States Patent [19]

Theissing et al.

[11] Patent Number: 5,153,015

[45] Date of Patent: Oct. 6, 1992

[54] DECAFFEINATING COFFEE AND TEA

[75] Inventors: Peter Theissing, Dortmund; Peter Saamer, Iserlohn-Hennen; Jörg-Peter Körner, Hagen, all of Fed. Rep. of Germany

[73] Assignee: Uhde GmbH, Dortmund, Fed. Rep. of Germany

[21] Appl. No.: 815,895

[22] Filed: Dec. 31, 1991

Related U.S. Application Data

[63] Continuation of Ser. No. 752,963, Aug. 29, 1991, abandoned, which is a continuation of Ser. No. 545,765, Jun. 28, 1990, abandoned, which is a continuation of Ser. No. 377,794, Jul. 11, 1989, abandoned, which is a continuation of Ser. No. 180,705, Apr. 5, 1988, abandoned, which is a continuation of Ser. No. 942,970, Dec. 16, 1986, abandoned, which is a continuation-in-part of Ser. No. 664,708, Oct. 25, 1984, abandoned.

[30] Foreign Application Priority Data

Oct. 28, 1983 [DE] Fed. Rep. of Germany ....... 3339181

[51] Int. Cl.⁵ .............................................. A23F 3/34
[52] U.S. Cl. ................... 426/427; 426/425; 426/428; 422/276; 422/277
[58] Field of Search ...................... 426/425, 427, 428; 422/276, 277

[56] References Cited

U.S. PATENT DOCUMENTS

| | | | |
|---|---|---|---|
| 2,214,978 | 9/1940 | Teatini | 422/276 X |
| 2,375,550 | 5/1945 | Grossman | 426/427 X |
| 4,344,974 | 8/1982 | Sirtl | 426/427 X |
| 4,364,965 | 12/1982 | van der Stegen | 426/427 X |

Primary Examiner—Joseph Golian
Attorney, Agent, or Firm—Anderson Kill Olick & Oshinsky

[57] ABSTRACT

A process and apparatus for extracting ingredient substances from natural products by means of a pressurized fluid, particularly for decaffeinating tea leaves by means of carbon dioxide, wherein the ingredient substances are bound by an adsorbent, preferably activated carbon. The fluid is conducted through a product layer, the thickness of which in flow direction is small in comparision with that transversely of the flow direction and the fluid is passed through the product layer with changing, especially increasing, velocity. The apparatus includes a cylindrical high-pressure vessel with annular cylindrical baskets for accommodating the natural product and/or the adsorbent, and the gas flows from a cylindrical outer range to a cylindrical inner range. The time required for the treatment of leafy natural product is reduced, the flow paths of the fluid are shortened, thus diminishing the risk of clogging, and the fluid flow velocity is reduced.

1 Claim, 2 Drawing Sheets

DECAFFEINATING COFFEE AND TEA

This is a continuation application of Ser. No. 07/752,963, filed Aug. 29, 1991 abandoned, which is a continuation of application Ser. No. 07/545,765, filed Jun. 28, 1990, abandoned which in turn is a continuation of Ser. No. 07/377,794, filed Jul. 11, 1989, abandoned, which in turn is a continuation of Ser. No. 07/180,705, filed Apr. 5, 1988, abandoned, which in turn is a continuation of Ser. No. 06/942,970, filed Dec. 16, 1986, abandoned, which in turn is a continuation in part of Ser. No. 06/664,708, filed Oct. 25, 1984, abandoned.

BACKGROUND OF THE INVENTION

The invention relates to a process and apparatus for extracting ingredient substances from natural products by means of a pressure fluid, particularly for decaffeinating tea leaves by means of carbon dioxide, wherein the ingredient substances are bound by an adsorbent, preferably activated carbon.

It is known to introduce, e.g., tea leaves in a high-pressure vessel through which pressurized carbon dioxide is conducted in axial direction. The effluent carbon dioxide is fed to a separate adsorber for binding the caffeine. Furthermore, it is known to recycle the carbon dioxide for this purpose.

The known procedure involves considerable disadvantages. Thus, very slender and long vessels have to be used for stability reasons which results in enormous dumping heights. This, in turn, leads to extended extraction times because the carbon dioxide flow velocity has to be low. In such an arrangement, the first tea leaf layers in flow direction remain exposed to the carbon dioxide flow even when the caffeine has already been extracted. However, the process must be continued until the last tea leaf layers in flow direction have been treated. By the time this has happened, the carbon dioxide has also extracted the aroma from all the preceding layers.

Another disadvantage is that tea leaf layers tend to agglomerate when flow velocities are high. Moreover, the type of construction causes part of the ingredient substances dissolved in the gas to precipitate on the vessel wall as well as in pipes and valves and results in clogging. A further disadvantage is that, at a constant carbon dioxide flow velocity through the tea leaf layers, the decaffeination rate gradually decreases with increasing caffeine load in the carbon dioxide.

It is the primary object of the present invention to improve the process described above by reducing the time required for the treatment of the natural product. Another object of the invention is to shorten the flow path of the loaded fluid thereby diminishing the risk of clogging and, in particular, to reduce the fluid flow velocity.

SUMMARY OF THE INVENTION

In accordance with the invention, this object is met by a process which includes conducting pressurized fluid through a product layer, the thickness of which in flow direction is small in comparison with its extension transversely of the flow direction, wherein the fluid is passed through the product layer with changing, especially, increasing, velocity.

The natural products which may be treated with the process according to the invention are, for example, fruits, leaves, bark, roots, twigs, seeds, etc., in addition to tea and coffee. The constituents extracted from these natural products are, for example, ethereal oils, aromatic compounds, pigments, drugs, flavoring agents, etc.

The pressurized fluids used in the process according to the invention are $CO_2$, $NO_2$, $CH_4$, $C_2H_6$, $C_2H_4$, etc., or mixtures thereof, introduced under hypercritical or near critical conditions.

The invention makes it possible to use reduced layer thicknesses of the natural product so that the pressure drop is smaller. Simultaneously, agglomeration of the natural product in flow direction of the fluid is eliminated. A uniform penetration of the natural product, as well as substantially lower inlet flow velocities, can be achieved. By arranging several layers of the natural product and of the adsorbent in series, the quantity of the fluid to be recycled becomes smaller so that equipment dimensions and costs are reduced.

A further advantage of the invention is that the decrease of the extraction degree in flow direction to be expected at constant fluid velocity, is avoided by the fact that the increasing velocity in accordance with this invention causes the substance transfer coefficient and thus the decaffeination coefficient to rise, which results in a uniform extraction within, e.g., the tea leaf layer.

According to an embodiment of the invention, the loaded fluid or gas reaches the adsorbent immediately upon leaving the product layer. In this way, a pollution of the gas and any formation of deposits in the apparatus and in the piping system can be avoided. The recycled gas is always available in unloaded and clean condition.

It is advantageous if the fluid enters the layer of the natural product via a large inlet surface or boundary and leaves it via a substantially smaller outlet surface or boundary. This procedure permits use of construction of comparatively simple design, for example pressure vessels in which the fluid enters the vessel via a larger outer cylindrical surface and leaves it via a smaller inner cylindrical surface, so that the penetration area is reduced.

According to the invention, provision may also be made for the fluid passing alternately through a product layer and an adsorbent, through another product layer and another adsorbent, etc., the process taking place either in separate units arranged in series or in a single unit containing all the layers.

The apparatus used for performing the process according to the invention includes a cylindrical high-pressure vessel with annular cylindrical baskets for accommodating the natural product and/or the adsorbent, wherein the gas flows from an outer cylindrical range to an inner cylindrical range. This equipment is of simple construction; it is especially suitable for high pressures and offers a safe and reliable flow of the gas.

According to an embodiment of the present invention, the cylindrical high-pressure vessel is equipped with a gastight bottom and a gastight cover, and a narrow annular gap exists between the outer basket for accommodating the natural product and the inner surface of the wall of the cylindrical vessel to create a cylindrical gas distribution surface, wherein the gas leaves the natural product and the adsorbent is discharged through a cylindrical inner space of the apparatus. The apparatus in accordance with this embodiment has an extremely compact structural size. Also, the product can easily be filled in and removed, and the adsorbent easily be replaced.

According to a further embodiment of the invention, several baskets for accommodating the natural product and the adsorbent may be arranged concentrically in the vessel. It is best to arrange cylindrical baskets for the natural product alternatingly with baskets for the adsorbent.

The invention also provides that the gas inlet wall can be equipped with baffles, holes, etc. for obtaining a uniform gas flow through the natural product and through the adsorbent.

After the gas leaves the natural product layer, a uniform distribution is achieved by the adsorbent layer, which also leads to a pressure equalization within the apparatus. If the effect obtained is not sufficient, a partition wall provided with holes, baffles, etc. may be installed between the layers of the natural product and of the adsorbent.

The process and apparatus according to the invention may also be used for the treatment of natural products other than tea and coffee, possibly without adsorbent layer if the extract is subjected to a further treatment. The extraction of rose oil shall be mentioned as an example in this connection.

A further embodiment of the present invention provides for the adsorbent being accommodated in an inner basket and the natural product being filled into the annular space between the adsorbent and the vessel lining which is at least over part of its length porous and permits penetration of the fluid. This embodiment offers particular advantages. Thus, the vessel design may be such that a common cover allows the cage accommodating the adsorbent, e.g., activated carbon, to be introduced centrally and the annular space to be filled with, e.g., coffee beans, etc. This considerably simplifies the construction.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention.

DETAILED DESCRIPTION OF THE PREFERRED EMBODIMENTS

Figure 1:
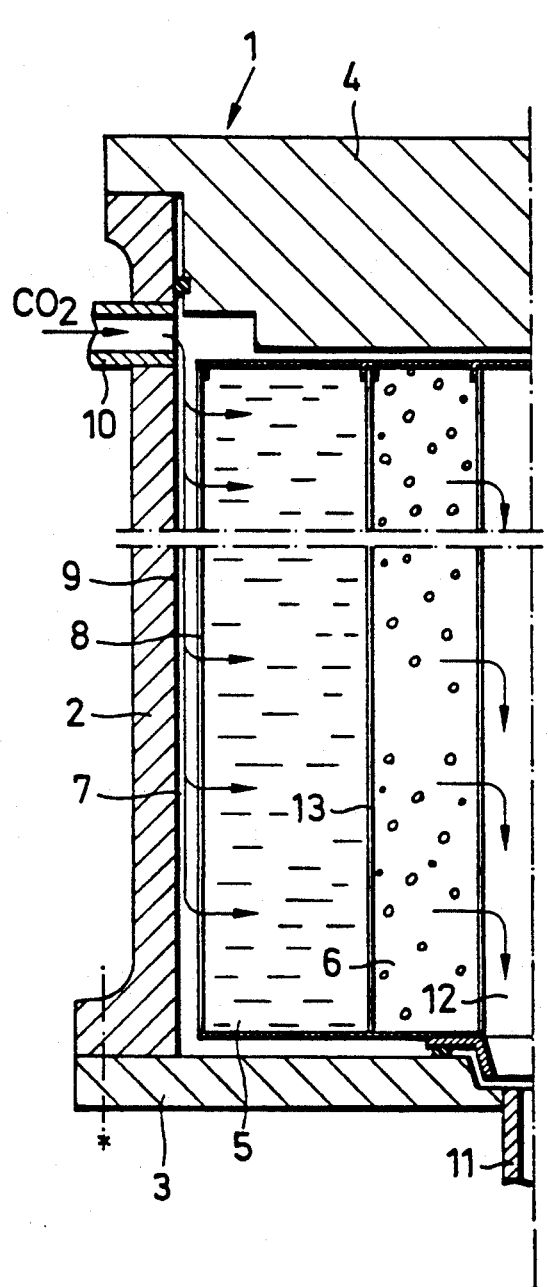
FIG. 1 is a cross-sectional view of the left part of an embodiment of the present invention.
Figure 2:
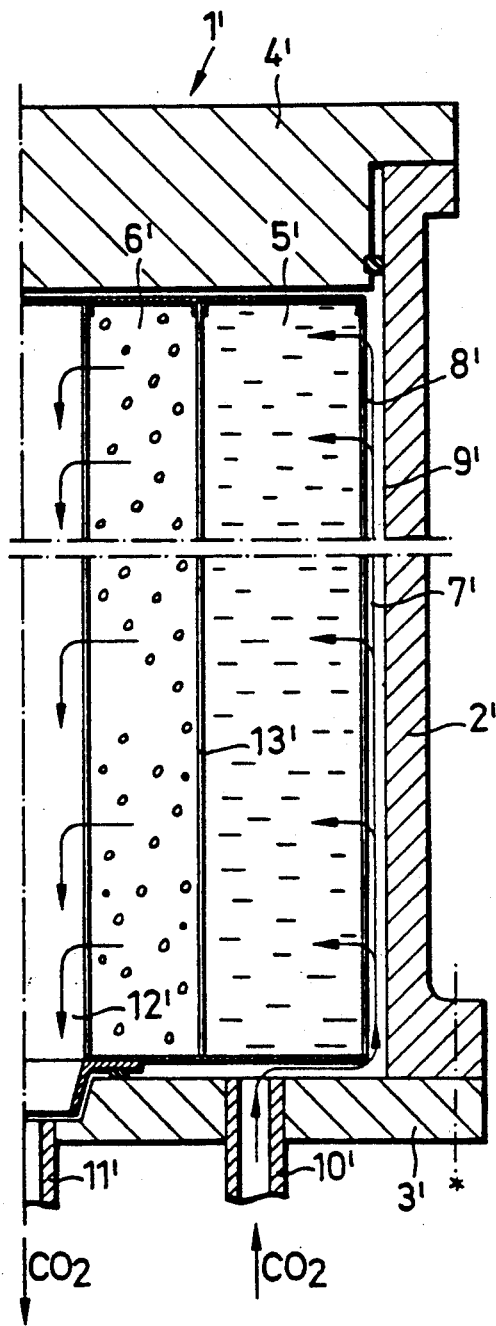
FIG. 2 is a cross-sectional view of the right part of another embodiment of the invention.

A high-pressure vessel, of which two different embodiments are shown in FIGS. 1 and 2, has been designated in FIG. 1 with 1 and in FIG. 2 with 1'. All components identical in function with those of FIG. 1 have, as far as possible, been provided with the same reference numerals in FIGS. 2 and 3. However, single primed numerals are used in FIG. 2 and double primed numerals in FIG. 3.

According to the embodiments shown in FIGS. 1 and 2, a cylindrical high-pressure vessel 1 includes a cylindrical shell 2 a bottom 3, and a cover 4, each attached in a gastight manner. It should be noted that, in practice, the cylindrical high-pressure vessel may have a length of 3 m or more.

The high-pressure vessel 1 has been equipped with annular cylindrical baskets 5 and 6 having perforated wall surfaces for accommodating the leafy natural product, e.g., tea, and the adsorbent, e.g., activated carbon. An annular space 7 is provided between the outer cylinder wall 8 of the basket 5 for the natural product and the inner surface of the high-pressure shell 9 to obtain a cylindrical distribution space for the process gas, e.g., carbon dioxide.

Carbon dioxide inlet nozzles 10 and 10' are located at the vessel shell 2 or in the bottom 3 of the high-pressure vessel, respectively. They may, of course, also be provided in the cover. However, the arrangement of the nozzles in the bottom or shell is more favorable because it is not necessary to remove supply lines for the purpose of opening the cover.

According to the embodiment shown in FIG. 1, the carbon dioxide enters the annular cylindrical space 7 laterally, passes through the tea layer 5 and then through the adsorbent layer 6, is withdrawn via the discharge nozzle 11 and returned by a recycle pump, not shown, to the inlet nozzle 10.

According to the embodiment shown in FIG. 2, both the inlet nozzle 10' and the discharge nozzle 11' for the carbon dioxide have been provided for in the bottom 3'.

The cylindrical inner space for the discharge of the carbon dioxide has been denoted with reference numerals 12 and 12', respectively. The gas enters the tea layer 5 via a large inlet surface area 8 and leaves via a smaller outlet surface area 13. This results in the carbon dioxide being accelerated during its passage through the tea layer 5 which, in turn, results in the advantages described above.

FIGS. 1 and 2 do not show that both the natural product, e.g., tea leaves, rose petals, etc., and the adsorbent can be accommodated in several annular cylindrical baskets which, after removal of the cover 4, may be drawn out of the vessel 1. It is also not shown in FIGS. 1 and 2 that several annular cylindrical baskets containing the natural product and the adsorbent can be provided alternately within one vessel. Several high-pressure vessels may, of course, be arranged in series or in parallel, if this is deemed expedient.

Figure 3:
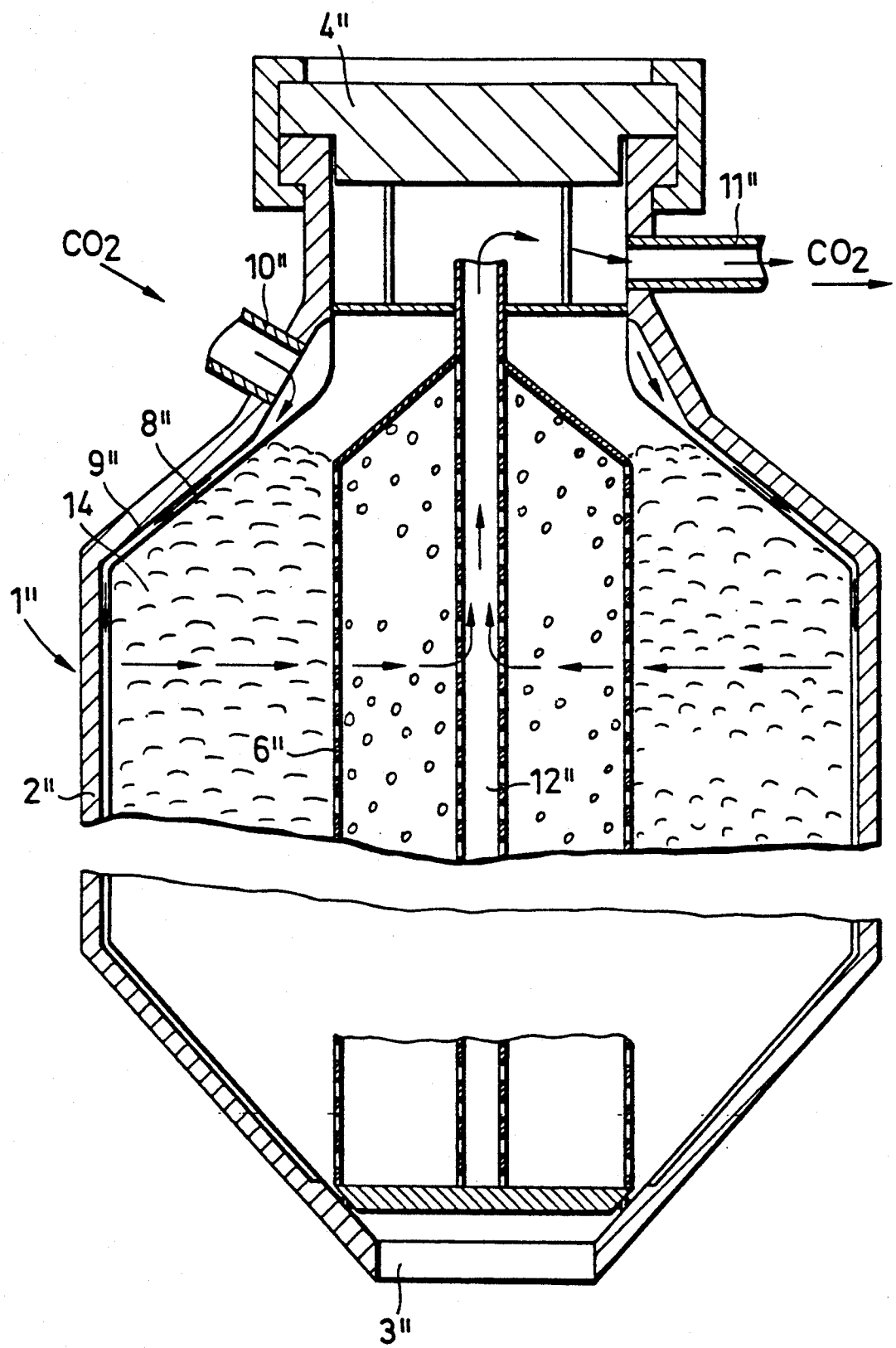
FIG. 3 is a cross-sectional view of a further embodiment of the invention.

According to the embodiment shown in FIG. 3, the high-pressure vessel 1" includes a cylinder 2" having two conical ends, the upper end being provided with a cover 4" and the lower end with an opening 3".

The cylinder wall 2" has been equipped on its inner surface 9" with a porous lining 8" which allows the penetration of, e.g., carbon dioxide into the interior of the vessel 1".

The dimensions of the basket 6" provided centrally in the vessel for accommodating the activated carbon are such as to allow the basket to be drawn out after removal of the cover 4". The bottom of this basket is self-sealing, so that the vessel 1" does not require any additional closure for the bottom 3". In the figure shown, the annular space 14 between the vessel wall lining 8" and the basket 6" for the activated carbon has been filled with coffee beans. The carbon dioxide inlet nozzle has been marked with 10" and the discharge nozzle for the loaded carbon dioxide with 11". The discharge nozzle 11" communicates with the cylindrical inner space 12" provided within the basket 6" for the gas discharge (see directional arrows).

The invention is not limited to the embodiments shown. Thus, the basket for accommodating the natural product could be arranged inside the vessel while the adsorbent would be placed in a separate device outside the vessel 1. Even the cylindrical type of construction is not the only possibility for realizing the invention. A number of box-type baskets with reduced cross-sections in flow direction migh also be used for being accommodated in a casing, etc.

To obtain a uniform distribution of the process gas, the inlet wall 8 may be provided with baffles, holes, etc. A uniform distribution of the gas inlet flow may also be achieved by choosing a conical form for the gas inlet space 7.

In operating the apparatus according to the invention, best results are obtained if the tea to be decaffeinated has a moisture content of 35% by weight. The process is carried out for a duration of 30 minutes under a pressure of 400 bar and a temperature of 70° C.

If a batch of 50 kg tea having a moisture content of 6% by weight is to be decaffeinated, the tea is moistened until it has a moisture content of 35% by weight. The batch of tea now has a weight of 72.3 kg. The basket 5 into which the tea is introduced has an axial length of 1.95 meters, an outer diameter of 0.42 meters and an inner diameter of 0.228 meters. The basket 6 containing the activated carbon has an outer diameter of 0.224 meters and an inner diameter of 0.087 meters. The resulting volumes of the baskets 5 and 6 are 0.19 meter$^3$ and 0.065 meters$^3$, respectively. $H_2O$-saturated $CO_2$ is introduced into vessel 1 at a rate of 30,000 kg/h.

The resulting $CO_2$ mass velocity at the outer boundary of the basket 5 is 11,666 kg/m$^2$/h and $CO_2$ mass velocity at the inner boundary of the basket 5 is 21,465 kg/m$^2$/h.

What is claimed is:

1. A process for extracting caffeine from a natural product selected from the group consisting of coffee and tea, comprising the steps of introducing a pressurized fluid selected from the group consisting of $CO_2$, $NO_2$, $CH_4$, $C_2H_6$ and $C_2H_4$ into an annular space formed between a cylindrical wall of a high-pressure vessel and a cylindrical outer perforated wall of a first basket containing the natural product, conducting the fluid through the natural product present in a layer formed between the outer wall of the first basket and an outer perforated wall of the second annular basket containing activated carbon as an adsorbent, the fluid being conducted through the product layer transversely of the axial direction of the first basket, whereby the velocity of the fluid increases as the fluid flows from the outer wall of the first basket toward the outer wall of the second basket, conducting the fluid through the adsorbent layer between the outer wall of the second basket and the inner wall of the second basket, and withdrawing the fluid from the cylindrical space defined within the high-pressure vessel by the inner wall of the second basket.

* * * * *